United States Patent [19]

Zhuang et al.

[11] Patent Number: 5,994,571
[45] Date of Patent: Nov. 30, 1999

[54] SUBSTITUTED ETHYLENE PRECURSOR AND SYNTHESIS METHOD

[75] Inventors: Wei-Wei Zhuang; Tue Nguyen; Lawrence J. Charneski, all of Vancouver, Wash.; David Russell Evans, Beaverton, Oreg.; Sheng Teng Hsu, Camas, Wash.

[73] Assignee: Sharp Laboratories of America, Inc., Camas, Wash.

[21] Appl. No.: 09/215,921

[22] Filed: Dec. 18, 1998

Related U.S. Application Data

[60] Provisional application No. 60/107,892, Nov. 10, 1998.

[51] Int. Cl.$^6$ .............................. C07F 1/08; C07F 15/00; C23C 16/00
[52] U.S. Cl. ....................... 556/117; 556/136; 427/587; 427/593
[58] Field of Search .................................. 556/117, 136; 427/587, 593

[56] References Cited

U.S. PATENT DOCUMENTS

| | | | |
|---|---|---|---|
| 4,385,005 | 5/1983 | Doyle | 260/464 |
| 4,425,281 | 1/1984 | Doyle | 260/430 |
| 4,434,317 | 2/1984 | Doyle et al. | 585/845 |
| 5,028,724 | 7/1991 | Ivankovits et al. | 556/40 |
| 5,085,731 | 2/1992 | Norman et al. | 156/646 |
| 5,096,737 | 3/1992 | Baum et al. | 427/38 |
| 5,144,049 | 9/1992 | Norman et al. | 556/12 |
| 5,441,766 | 8/1995 | Choi et al. | 427/250 |

OTHER PUBLICATIONS

Article entitled, "Low–Temperature Chemical Vapor Deposition of High–Purity Copper from an Organometallic Source" by D.B. Beach, F. K. LeGoues & Cheo–Kun Hu, published in 1990 American Chemical Society, Chem., Mater. 1990, 2, pp. 216–219.

Article entitled, "Hot–Wall Chemical Vapor Deposition of Copper from Copper(I) Compounds, etc,", by H.K. Shin, K.M. Chi, M.J. Hampden–Smith, T.T. Kodas, J.D. Farr and M. Paffett, published in 1992 American Chemical Society, Chem. Mater. 1992,4, pp. 788–795.

Article entitled, "Alkene and Carbon Monoxide Derivatives of Copper(I) and Silver(I) B–Diketonates", by G. Doyle, K.A. Eriksen and D. Van Engen, published in Organometallics 1985, 4, pp. 830–835.

Article entitled, "Copper(I) tert–Butyl 3–Oxobutanoate Complexes as Precursors for Chemical Vapor Deposition of Copper", by H. Choi and S. Hwang, published in 1998 American Chemical Society, Chem. Mat. 1998, 10, pp. 2326–2328.

Article entitled, "Chemical Vapor Deposited Copper from Alkyne Stabilized Copper(I) Hexafluoracetylacetonated Complexes", by T. H. Baum and C. E. Larson, published in J. Electrochem. Soc. vol. 140, No. 1, Jan. 1993, pp. 154–158.

*Primary Examiner*—Porfirio Nazario-Gonzalez
*Attorney, Agent, or Firm*—Gerald Maliszewski; David C. Ripma

[57] ABSTRACT

A Cu(hfac) precursor with a substituted ethylene ligand has been provided. The substituted ethylene ligand includes bonds to molecules selected from the group consisting of $C_1$ to $C_8$ alkyl, $C_1$ to $C_8$ haloalkyl, H, and $C_1$ to $C_8$ alkoxyl. One variation, the 2-methyl-1-butene ligand precursor has proved to be stable at room temperature, and extremely volatile at higher temperatures. Copper deposited with this precursor has low resistivity and high adhesive characteristics. Because of the volatility, the deposition rate of copper deposited with this precursor is very high. A synthesis method has been provided which produces a high yield of the above-described precursor.

19 Claims, 2 Drawing Sheets

SUBSTITUTED ETHYLENE PRECURSOR AND SYNTHESIS METHOD

This invention claims the benefit of a provisional application Ser. No. 60/107,892, filed Nov. 10, 1998, entitled "Improved Copper Precursor and Synthesis Method", having the same inventors as the present application.

BACKGROUND AND SUMMARY OF THE INVENTION

This invention relates generally to integrated circuit processes and fabrication, and more particularly, to a precursor and synthesis method, having a substituted ethylene ligand, such as 2-methyl-1-butene, which improves liquid phase stability, and which is capable of depositing copper at high deposition rates, low resistivity, and with good adhesion on selected integrated circuit surfaces.

The demand for progressively smaller, less expensive, and more powerful electronic products, in turn, fuels the need for smaller geometry integrated circuits (ICs) on larger substrates. It also creates a demand for a denser packaging of circuits onto IC substrates. The desire for smaller geometry IC circuits requires that the interconnections between components and dielectric layers be as small as possible. Therefore, research continues into reducing the width of via interconnects and connecting lines. The conductivity of the interconnects is reduced as the area of the interconnecting surfaces is reduced, and the resulting increase in interconnect resistivity has become an obstacle in IC design. Conductors having high resistivity create conduction paths with high impedance and large propagation delays. These problems result in unreliable signal timing, unreliable voltage levels, and lengthy signal delays between components in the IC. Propagation discontinuities also result from intersecting conduction surfaces that are poorly connected, or from the joining of conductors having highly different impedance characteristics.

There is a need for interconnects and vias to have both low resistivity, and the ability to withstand process environments of volatile ingredients. Aluminum and tungsten metals are often used in the production of integrated circuits for making interconnections or vias between electrically active areas. These metals are popular because they are easy to use in a production environment, unlike copper which requires special handling.

Copper (Cu) would appear to be a natural choice to replace aluminum in the effort to reduce the size of lines and vias in an electrical circuit. The conductivity of copper is approximately twice that of aluminum and over three times that of tungsten. As a result, the same current can be carried through a copper line having nearly half the width of an aluminum line.

The electromigration characteristics of copper are also much superior to those of aluminum. Aluminum is approximately ten times more susceptible than copper to degradation and breakage due to electromigration. As a result, a copper line, even one having a much smaller cross-section than an aluminum line, is better able to maintain electrical integrity.

There have been problems associated with the use of copper, however, in IC processing. Copper pollutes many of the materials used in IC processes and, therefore barriers are typically erected to prevent copper from migrating. Elements of copper migrating into these semiconductor regions can dramatically alter the conduction characteristics of associated transistors. Another problem with the use of copper is the relatively high temperature needed to deposit it on, or removing it from, an IC surface. These high temperatures can damage associated IC structures and photoresist masks.

It is also a problem to deposit copper onto a substrate, or in a via hole, using the conventional processes for the deposition of aluminum when the geometries of the selected IC features are small. That is, new deposition processes have been developed for use with copper, instead of aluminum, in the lines and interconnects of an IC interlevel dielectric. It is impractical to sputter metal, either aluminum or copper, to fill small diameter vias, since the gap filling capability is poor. To deposit copper, first, a physical vapor deposition (PVD), and then, a chemical vapor deposition (CVD) technique, have been developed by the industry.

With the PVD technique, an IC surface is exposed to a copper vapor, and copper is caused to condense on the surfaces. The technique is not selective with regard to surfaces. When copper is to be deposited on a metallic surface, adjoining non-conductive surfaces must either be masked or etched clean in a subsequent process step. As mentioned earlier, photoresist masks and some other adjoining IC structures are potentially damaged at the high temperatures at which copper is processed. The CVD technique is an improvement over PVD because it is more selective as to which surfaces copper is deposited on. The CVD technique is selective because it is designed to rely on a chemical reaction between the metallic surface and the copper vapor to cause the deposition of copper on the metallic surface.

In a typical CVD process, copper is combined with a ligand, or organic compound, to help insure that the copper compound becomes volatile, and eventually decomposes, at consistent temperatures. That is, copper becomes an element in a compound that is vaporized into a gas, and later deposited as a solid when the gas decomposes. Selected surfaces of an integrated circuit, such as diffusion barrier material, are exposed to the copper gas, or precursor, in an elevated temperature environment. When the copper gas compound decomposes, copper is left behind on the selected surface. Several copper gas compounds are available for use with the CVD process. It is generally accepted that the configuration of the copper gas compound, at least partially, affects the ability of the copper to be deposited on to the selected surface.

Copper metal thin films have been prepared via chemical vapor deposition by using many different kinds of copper precursors. In 1990, D. B. Beach et al. *Chem. Mater.* (2) 216 (1990) obtained pure copper films via CVD by using ($\eta^5$-$C_5H_5$)Cu(PMe$_3$), and later, in 1992, H. K. Shin et al., *Chem. Mater.* (4) 788 (1992) declared the same results by using (hfac)Cu(PR$_3$)$_n$ (R=methyl and ethyl and n=1 and 2). However, these copper precursors are solids, which can not be used in the liquid delivery system for copper thin film CVD processing. Furthermore, the copper films often contain contamination of carbon and phosphorus, which can not be used as interconnectors in microprocessors.

$Cu^{2+}$ (hfac)$_2$, or copper (II) hexafluoroacetylacetonate, precursors have previously been used to apply CVD copper to IC substrates and surfaces. However, these $Cu^{2+}$ precursors are notable for leaving contaminates in the deposited copper, and for the relatively high temperatures that must be used to decompose the precursor into copper.

The studies of copper precursors conducted in the early of 1990's were concentrated on the evaluation of a series of copper(I) fluorinated β-diketonate complexes, which have been proven to be very promising sources for the use in the chemical vapor deposition of copper metal thin films.

Copper(I) fluorinated β-diketonate complexes were first synthesized by Gerald Doyle, U.S. Pat. No. 4,385,005 (1983) and U.S. Pat. No. 4,425,281 (1984), in which he presented the synthesis method and their application in the separation of unsaturated organic hydrocarbons. In the U.S. Pat. No. 5,096,737 (1992), Thomas H. Baum, et at., claimed the application of these copper(I) fluorinated β-diketonate complexes as copper precursors for CVD copper thin film preparation. Copper thin films have been prepared via chemical vapor deposition using these precursors.

Among several liquid copper precursors, 1,5-dimethyl 1,5-cyclooctadiene copper(I) hexafluoroacetylacetonate mixed with 1,6-dimethyl 1,5-cyclooctadiene copper(I) hexafluoroacetylacetonate ((DMCOD)Cu(hfac)) and hexyne copper(I) hexafluoroacetylacetonate ((HYN)Cu(hfac)) were evaluated in detail. The copper thin films deposited using (DMCOD)Cu(hfac) have very good adhesion to metal or metal nitride substrates, but a high resistivity (2.5 $\mu\Omega$·cm) and a low deposition rate. (HYN)Cu(hfac) copper film has poor adhesion to a TiN substrate, and high resistivity (~2.1 $\mu\Omega$·cm). Another compound, butyne copper(I)(hfac), ((BUY)Cu(hfac)), gives a copper film with low resistivity (1.93 $\mu\Omega$ cm), but has poor adhesion and is relatively expensive. Also, the compound is a solid and, therefore, difficult to use in a liquid delivery system. The invention of copper(I)(hfac) stabilized with a series of trialkylvinylsilane (John A. T. Norman et al., U.S. Pat. No. 5,085,731 (1992)) improved the properties of copper thin films.

Copper films deposited using a liquid copper precursor, (hfac)Cu(TMVS), where TMVS=trimethylvinylsilane, have low resistivities and reasonably adhesion to substrates. This precursor is useful because it can be used at relatively low temperatures, approximately 200° C. This liquid copper precursor has been used for the preparation of copper metal thin films via CVD for some time, but there are still some drawbacks: stability, the adhesion of copper films, and cost for the trimethylvinylsilane stabilizer. Also, the precursor is not especially stable, and can have a relatively short shelf life if not refrigerated. Various ingredients have been added to (hfac)Cu(tmvs) to improve its adhesiveness, temperature stability, and the rate at which it can be deposited on an IC surface. U.S. Pat. No. 5,744,192, entitled "Method Of Using Water To Increase The Conductivity Of Copper Deposited With Cu(HFAC)TMVS", invented by Nguyen et al., discloses a precursor and method of improving the electrical conductivity of Cu deposited with (hfac)Cu(tmvs).

It is generally acknowledged in the industry that (hfac) Cu(tmvs) becomes unstable, and begins to decompose, above 35° C. Use of a (hfac)Cu(tmvs) precursor stored at this temperature leads to undesirable process results. The effectivity of (hfac)Cu(tmvs) stored at temperatures lower than 35° C. is also unpredictable. A "fresh" batch of precursor, or precursor stored at temperatures well below room temperature, is used to guarantee predictable processes.

A Cu precursor comprising a ligand of methoxy and methyl groups is disclosed in co-pending application Ser. No. 08/779,640, filed Jan. 7, 1997, entitled "Precursor with (Methoxy)(methyl)silylolefin Ligands to Deposit Cu and Method for Same", invented by Senzaki et al., and assigned to the same assignee as the instant patent. The disclosed precursor permits either one or two methoxy groups to be bonded to the silicon atom of the ligand. That is, the precursor can be "fine tuned" using ligands having more methoxy groups than tmvs, but less than tmovs are provided. The oxygen atoms in the methoxy groups contribute electrons to the Cu atoms, to strengthen the Cu-olefin bond, and so, prevent the premature decomposition of the precursor in storage, or as the precursor is heated for the application of Cu to an IC surface. However, only hydrocarbon groups of one carbon atom, $CH_3$ (methyl) and $OCH_3$ (methoxy), are disclosed.

A Cu precursor comprising a ligand of alkyl and alkyl groups is disclosed in U.S. Pat. No. 5,767,301, entitled "Precursor with (Alkyloxy)(Alkyl)silylolefin Ligands to Deposit Copper", invented by Senzaki et al. The disclosed precursor describes alkyl groups bonded to the silicon atom of the ligand with alkoxyl groups. However, the search continues for even more effective copper precursors.

A Cu precursor comprising a ligand of a substituted phenylethylene ligand is disclosed in co-pending application Ser. No. 09/210,099, entitled "Substituted Phenylethylene Precursor and Synthesis Method", invented by Zhuang et al., and filed on Dec. 11, 1998. The disclosed precursor is practical for use in the deposition of CVD copper, but more volatile precursors are also desirable.

It would be advantageous if a copper precursor was found that effectively deposits copper with low resistivity and good adhesion properties.

It would be advantageous if an extremely volatile precursor was found to deposit low resistivity copper at high deposition rates.

It would be advantageous if a method were found of making a Cu(hfac) precursor stable over a wider range of temperatures, and to provide that the precursor remain in liquid phase during storage.

It would also be advantageous if water, H-hfac, H-hfac dihydrate (H-hfac·2H$_2$O) were no longer necessary to blend with a Cu precursor to improve the thermal stability of the Cu precursor.

Accordingly, a volatile metal (M) precursor compound for the chemical vapor deposition (CVD) of metal to selected surfaces is provided. The metal is selected from the group consisting of copper (Cu), silver (Ag), and iridium (Ir). The precursor compound comprises:

$M^{+1}$ (hexafluoroacetylacetonate); and a substituted ethylene ligand with a first carbon atom including a first and second bond. The first and second bonds are selected from groups independent of each other. The first bond is selected from a group consisting of $C_1$ to $C_8$ alkyl, $C_1$ to $C_8$ haloalkyl, and $C_1$ to $C_8$ alkoxyl. The second bond is selected from a group consisting of H, $C_1$ to $C_8$ alkyl, $C_1$ to $C_8$ haloalkyl, and $C_1$ to $C_8$ alkoxyl. A second carbon atom includes a third and fourth bond. The third and fourth bonds are selected, independent of each other, from the group consisting of H, $C_1$ to $C_8$ alkyl, $C_1$ to $C_8$ haloalkyl, and $C_1$ to $C_8$ alkoxyl. In this manner, a stable precursor capable of high metal deposition rates is formed.

Preferably, the first bond is $CH_3$, the second bond is $CH_2CH_3$, and the third and fourth bonds are H, whereby an 2-methyl-1-butene ligand is formed.

In some aspects of the invention the compound includes an additive to create a precursor blend, and in which the precursor blend further comprises:

less than approximately 10% substituted ethylene, as measured by weight ratio of the precursor compound, to facilitate a stable liquid phase precursor. Preferably, the precursor blend further comprises approximately 5.04% substituted ethylene, as measured by weight ratio of the precursor compound.

A method for synthesizing a metal(hfac) [M(hfac)] substituted ethylene precursor is also provided comprising the steps of:

a) forming a uniformly mixed solution of $M_2O$ in a solvent, preferably the metal is selected from the group consisting of copper and silver;

b) introducing a substituted ethylene to the solution of Step a), and forming a uniformly mixed solution, preferably the substituted ethylene is 2-methyl-1-butene;

c) introducing hexafluoroacetylacetone (hfac) to the solution of Step b), and forming a uniformly mixed solution;

d) filtering the solution to remove solid materials, whereby any excess $M_2O$ is removed;

e) removing the solvent from the solution; and f) filtering to remove the solid material, whereby a liquid phase precursor is formed.

One aspect of the invention includes a further step, following Step e), and preceding Step f), of:

$e_1$) adding less than approximately 10%, by weight ratio, of the substituted ethylene used in Step b) to the solution, whereby the liquid phase stability of the precursor is improved. Preferably, Step $e_1$) includes adding approximately 5.04% substituted ethylene.

DETAILED DESCRIPTION OF THE PREFERRED EMBODIMENT

The substituted ethylene ligand copper precursor, disclosed below, is inexpensive to synthesize. The precursor is stable at room temperature for easy storage and handling. Despite retaining its liquid phase at room temperature, it is highly volatile at higher temperatures. Therefore, no decomposition occurs in the CVD liquid delivery line and vaporizer. Further, the precursor has excellent adhesion to metal and metal nitride substrates, such as W, Ti, TiN, Ta, TaN, Al, Pt, WN, and similar barrier materials. The copper deposited with precursor has low resistivity (<1.9 $\mu\Omega\cdot$cm), high electromigration resistance, and excellent conformality to severe surface morphology.

Figure 1:
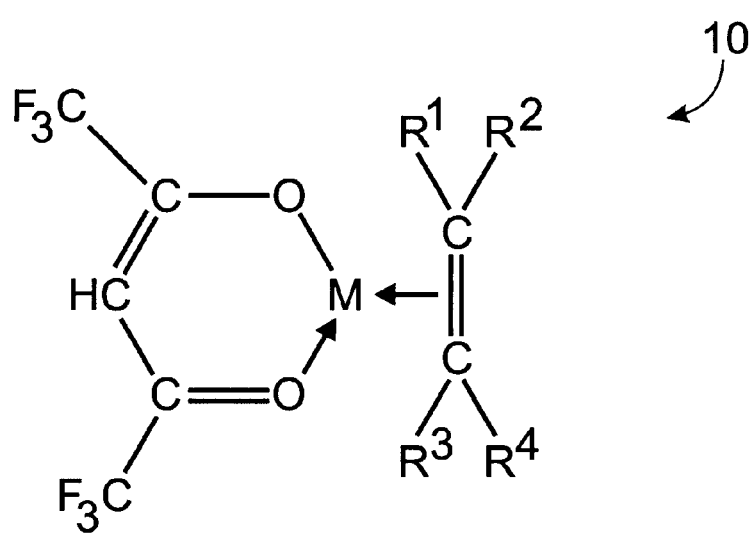
FIG. 1 is a schematic representation of the present invention precursor with a substituted ethylene ligand.

FIG. 1 is a schematic representation of the present invention precursor with a substituted ethylene ligand. Volatile metal (M) precursor compound 10 is used for the chemical vapor deposition (CVD) of metal (M) to selected surfaces. The metal is selected from the group consisting of copper (Cu), silver (Ag), and iridium (Ir). Precursor compound 10 comprises $M^{+1}$(hexafluoroacetylacetonate) and a substituted ethylene ligand.

Figure 2:
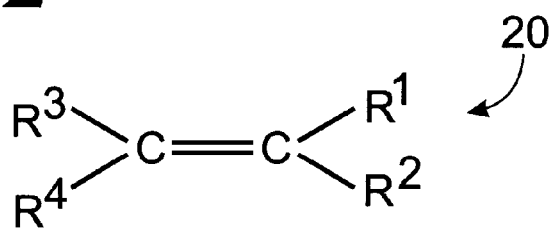
FIG. 2 is a schematic representation of a substituted ethylene ligand.

FIG. 2 is a schematic representation of substituted ethylene ligand 20. Substituted ethylene ligand 20 comprises a first carbon atom including a first and second bond. The first bond is selected from a group consisting of $C_1$ to $C_8$ alkyl, $C_1$ to $C_8$ haloalkyl, and $C_1$ to $C_8$ alkoxyl. The second bond is selected from a group consisting of H, $C_1$ to $C_8$ alkyl, $C_1$ to $C_8$ haloalkyl, and $C_1$ to $C_8$ alkoxyl. Substituted ethylene ligand 20 also comprises a second carbon atom including a third and fourth bond. The third and fourth bonds are selected from the group consisting of H, $C_1$ to $C_8$ alkyl, $C_1$ to $C_8$ haloalkyl, and $C_1$ to $C_8$ alkoxyl. In this manner, a stable precursor capable of high metal deposition rates is formed. The first ($R^1$), second ($R^2$), third ($R^3$), and fourth ($R^4$) vary independently from each other. That is, the choice of an specific R group is not dependent on the specific choice of any other R group.

Figure 3:
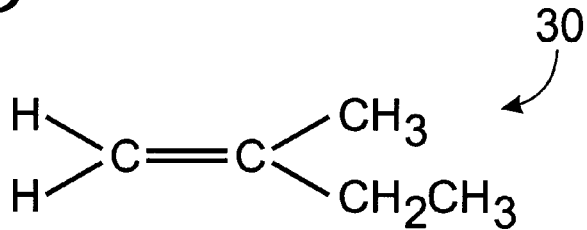
FIG. 3 is a schematic representation of the preferred embodiment 2-methyl-1-butene ligand.

FIG. 3 is a schematic representation of the preferred embodiment 2-methyl-1-butene ligand 30. First bond ($R^1$) is $CH_3$, the second bond ($R^2$) is $CH_2CH_3$, the third bond ($R^3$) is H, and the fourth bond ($R^4$) is H. In this manner, a 2-methyl-1-butene ligand is formed.

To improve and facilitate a stable liquid phase precursor, in some aspects of the invention, compound 10 includes an additive to create a precursor blend. The precursor blend further comprises less than approximately 10% substituted ethylene 20 (see FIG. 2), as measured by weight ratio of the precursor compound. Preferably, the precursor blend further comprises approximately 5.04% substituted ethylene, as measured by weight ratio of the precursor compound, to facilitate a stable liquid phase precursor.

Volatile metal (M) precursor compound 10, with the metal selected from the group consisting of copper, silver, and iridium, is alternately represented with the following structural formula:

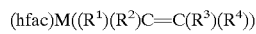

in which $R^1$ is selected from the group consisting of $C_1$ to $C_8$ alkyl, $C_1$ to $C_8$ haloalkyl, and $C_1$ to $C_8$ alkoxyl;

in which $R^2$ is selected from the group consisting of H, $C_1$ to $C_8$ alkyl, $C_1$ to $C_8$ haloalkyl, and $C_1$ to $C_8$ alkoxyl;

in which $R^3$ is selected from the group consisting of H, $C_1$ to $C_8$ alkyl, $C_1$ to $C_8$ haloalkyl, and $C_1$ to $C_8$ alkoxyl; and in which $R^4$ is selected from the group consisting of H, $C_1$ to $C_8$ alkyl, $C_1$ to $C_8$ haloalkyl, and $C_1$ to $C_8$ alkoxyl, whereby a precursor is formed from a substituted ethylene ligand.

Preferably, $R^1$ is $CH_3$, in which $R^2$ is $CH_2CH_3$, $R^3$ is H, and $R^4$ is H, whereby an 2-methyl-1-butene ligand is formed.

In some aspects of the invention, the compound includes an additive to create a metal precursor blend. The blend further comprising the substituted ethylene has the following structural formula:

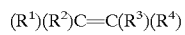

in which $R^1$ is selected from the group consisting of $C_1$ to $C_8$ alkyl, $C_1$ to $C_8$ haloalkyl, and $C_1$ to $C_8$ alkoxyl; and in which $R^2$, $R^3$, and $R^4$ are selected from the group consisting of H, $C_1$ to $C_8$ alkyl, $C_1$ to $C_8$ haloalkyl, and $C_1$ to $C_8$ alkoxyl. In this manner, the precursor is further stabilized in a liquid phase. Preferably, $R^1$ is $CH_3$, in which $R^2$ is $CH_2CH_3$, and $R^3$ and $R^4$ are H, whereby an 2-methyl-1-butene is formed.

The combined additive is less than approximately 10% by weight ratio of the precursor blend. Preferably, the additive is 2-methyl-1-butene, at approximately 5.04% by weight of the precursor blend. Further, the substituted ethylene ligand selected to form the precursor is the same substituted ethylene ligand used as the additive to from the precursor blend.

The prior art (Doyle) synthesis procedures proved unsatisfactory in the synthesis of the substituted ethylene copper precursor. The reaction between $Cu_2O$, 1,1,1,5,5,5- hexafluoroacetylacetone and 2-methyl-1-butene, in making 2-methyl-1-butene copper(I) hexafluoroacetylacetonate ((2M1B)Cu(hfac)) in dichloromethane, produces a liquid product that is not stable at room temperature for long periods of time. To remedy this situation, the published synthesis route was modified.

Figure 4:
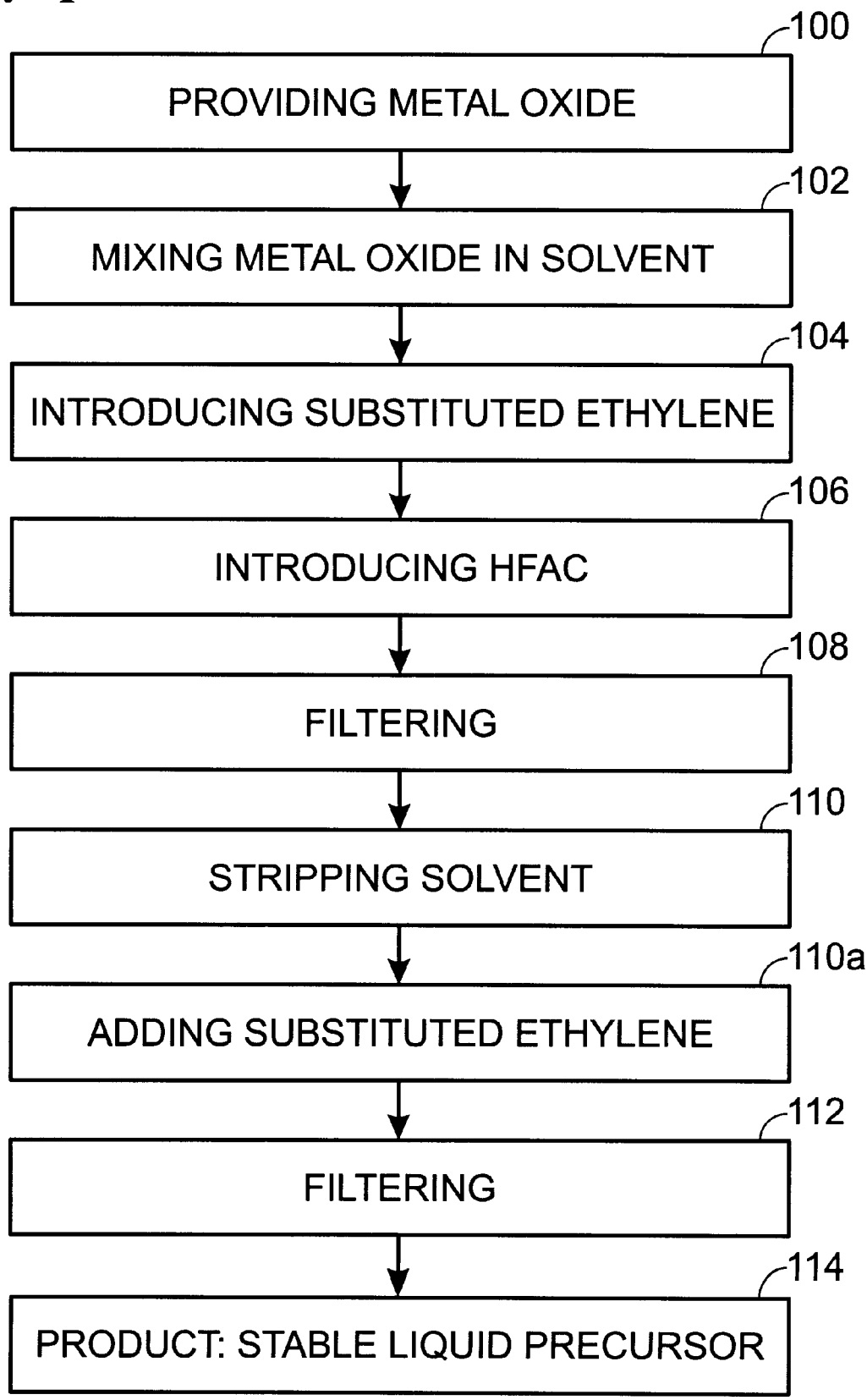
FIG. 4 is a flowchart illustrating steps in a method for synthesizing a copper(hfac) substituted ethylene precursor.

FIG. 4 is a flowchart illustrating steps in a method for synthesizing a metal(hfac) [M(hfac)] substituted ethylene precursor. Step 100 provides $M_2O$. The metal is selected from the group consisting of copper and silver. Precursor synthesis procedures specific to iridium are still in development. Step 102 forms a uniformly mixed solution of $M_2O$ in a solvent. Step 102 includes using a solvent selected from the group consisting of dichloromethane and tetrahydrofuran (THF), although dichloromethane is preferred. Step 104 introduces a substituted ethylene to the solution of Step 102, and forms a uniformly mixed solution. In the preferred embodiment, Step 104 includes the substituted ethylene being 2-methyl-1-butene. Step 106 introduces hexafluoroacetylacetone (hfac) to the solution of Step 104, and forms a uniformly mixed solution.

Step 108 filters the solution to remove solid materials, whereby any excess $M_2O$ is removed. It is typical to add excess $M_2O$ in Step 102 of the procedure. $M_2O$ is inexpensive and an excess amount produces a higher yield of precursor. At this step in the process other solids such as impurities are removed. In some aspects of the invention celite ($SiO_2$) is used to filter the solution. Often celite is used in addition to a ceramic filter having pore diameters in the range between 10 and 25 microns. Therefore, Step 108 includes removing solid material larger than approximately 25 microns.

Step 110 removes the solvent from the solution. Step 112 filters to remove the solid material. Step 112 includes filtering solid material having a size greater than approximately 1 micron. In small batches, a 1 micron size filter on a syringe opening, was used to extract the solution. Step 114 is a product, a liquid phase precursor.

In some aspects of the invention, Step 102 includes the $M_2O$ being, in proportion, 0.120 mol, Step 104 includes the substituted ethylene being, in proportion, 0.170 mol, and Step 106 includes the hfac being, in proportion, 0.170 mol. By maintaining the above-described proportions, precursor is made in batches of any size.

In some aspects of the invention, a further step follows Step 110. Step 110*a* adds less than approximately 10%, by weight ratio, of the substituted ethylene used in Step 104 to the solution, whereby the liquid phase stability of the precursor is improved. Preferably, Step 110*a* includes adding approximately 5.04% of a substituted ethylene such as 2-methyl-1-butene. The ligand introduced in Step 104, is the same ligand added in Step 110*a*.

All manipulations were carried out in an air-free dry glovebox or by using standard Schlenk techniques. Solvents were purified before synthesis. Dichloromethane was refluxed and distilled over calcium hydride under an atmosphere of nitrogen prior to use. 1,1,1,5,5,5-hexafluoroacetylacetone and 2-methyl-1-butene were purchased from Strem and Aldrich, respectively, and used directly without any purification.

The synthesis procedure of organometallic copper(I) complexes was first described by Doyle in U.S. Pat. No. 4,385,005, in which copper monoxide reacted with unsaturated organic hydrocarbon and 1,1,1,5,5,5-hexafluoroacetylacetone in dichloromethane or THF. The reaction is described by the following equation:

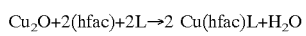

$$Cu_2O + 2(hfac) + 2L \rightarrow 2\ Cu(hfac)L + H_2O$$

where L is unsaturated organic hydrocarbon ligand.

According to the synthesis procedure above, the synthesis of (2M1B)Cu(hfac) gives the a product that is relatively unstable at room temperature. To improve the yield of liquid compound, Doyle's synthesis procedure was modified by introducing 5 to 10% extra 2-methyl-1-butene into reaction. By this modified synthesis procedure, pure liquid (2M1B) Cu(hfac) is obtained with a high yield.

In the synthesis of Cu(hfac)(2M1B), $M_2O$ (17.0 g, 0.12 mol) was added into a 100 ml round bottom flask equipped with $CH_2Cl_2$ (50 ml) and a stirring bar. To this $Cu_2O$ dichloromethane red solution, 2-methyl-1-butene (18.4 ml, 0.17 mol) was added and stirred at room temperature for ten minutes. Then 1,1,1,5,5,5-hexafluoroacetylacetone (24.1 ml, 0.17 mol) was slowly introduced into this red color solution with stirring. After 2 minutes, the solution color gradually changed to green. The green solution was continually stirred for another 10 minutes, and then filtered through celite. The green filtrate was stripped under vacuum for two hours and then heated to 35° C. under vacuum for another half-hour stripping. This produced a green liquid organometallic copper compound, which was then filtered through a fine filter (1 μm) to give 45.37 grams of product (yield: 78.24% based on hfac, and a theoretic yield based on hfac is 57.992 gram). For stabilization, 2-methyl-1-butene (2.41 g) was introduced into the product (total of 47.78 g), in which the product contained 5.04% free 2-methyl-1-butene.

The $^1H$ NMR structural analysis was carried out on a QE 300 MHz NMR instrument. The results are as follows: $^1H$ NMR ($CD_2Cl_2$) δ 1.15 (triplet, 3, $J_{HH}$=7.2 Hz, ($CH_3CH_2$) ($CH_3$)C=$CH_2$), 1.90 (s, 3, ($CH_3CH_2$)($CH_3$)C=$CH_2$), 2.20 (quartet, 2, $J_{HH}$=7.2 Hz, ($CH_3CH_2$)($CH_3$)C=$CH_2$), 4.22 (s, 1, ($CH_3CH_2$)($CH_3$)C=$CH_2$), 4.23 (s, 1, ($CH_3CH_2$)($CH_3$) C=$CH_2$), 6.12 (s, 1, $CF_3C(O)CHC(O)CF_3$).

A new and improved copper precursor, and synthesis method for the copper precursor, has been disclosed above. The precursor, especially the 2-methyl-1-butene ligand precursor, is stable a room temperature, and extremely volatile at higher temperatures. Copper deposited with the precursor has low resistivity and high adhesive characteristics. Finally, the precursor can be deposited at high deposition rates, because of the high volatility. A synthesis method has been disclosed which produces a high yield of the above-described precursor. Other variations and embodiments will occur to those skilled in the art.

What is claimed is:

1. A volatile metal (M) precursor compound for the chemical vapor deposition (CVD) of metal to selected surfaces, the precursor compound comprising:

$M^{+1}$(hexafluoroacetylacetonate); and a substituted ethylene ligand with a first carbon atom including a first and second bond, in which said first bond is $CH_3$, said second bond is $CH_2CH_3$, with a second carbon atom including a third and fourth bond, in which said third and fourth bonds are H, whereby an 2-methyl-1-butene ligand is formed.

2. A volatile metal (M) precursor compound for the chemical vapor deposition (CVD) of metal to selected surfaces, the precursor compound comprising:

$M^{+1}$ (hexafluoroacetylacetonate);

a substituted ethylene ligand with a first carbon atom including a first and second bond, said first bond being selected from a group consisting of $C_1$ to $C_8$ alkyl, $C_1$ to $C_8$ haloalkyl, and $C_1$ to $C_8$ alkoxyl, and said second bond being selected from a group consisting of H, $C_1$ to $C_8$ alkyl, $C_1$ to $C_8$ haloalkyl, and $C_1$ to $C_8$ alkoxyl, with a second carbon atom including a third and fourth bond, said third and fourth bonds being selected from the group consisting of H, $C_1$ to $C_8$ alkyl, $C_1$ to $C_8$ haloalkyl, and $C_1$ to $C_8$ alkoxyl, whereby a stable precursor capable of high metal deposition rates is formed; and in which the compound includes an additive to create a precursor blend, the precursor blend further comprising:

less than approximately 10% substituted ethylene, as measured by weight ratio of the precursor compound, to facilitate a stable liquid phase precursor.

3. A metal precursor as in claim 2 the precursor blend further comprises approximately 5.04% substituted ethylene, as measured by weight ratio of the precursor compound, to facilitate a stable liquid phase precursor.

4. A volatile metal (M) precursor compound for applying chemical vapor deposition (CVD) metal to selected surfaces, the precursor compound having the following structural formula:

$$(hfac)M((R^1)(R^2)C=C(R^3)(R^4))$$

in which $R^1$ is $CH_3$, in which $R^2$ is $CH_2CH_3$, and $R^3$ and $R^4$ are H, whereby an 2-methyl-1-butene is formed.

5. A volatile metal (M) precursor compound for applying chemical vapor deposition (CVD) metal to selected surfaces, the precursor compound having the following structural formula:

$$(hfac)M((R^1)(R^2)C=C(R^3)(R^4))$$

in which $R^1$ is selected from the group consisting of $C_1$ to $C_8$ alkyl, $C_1$ to $C_8$ haloalkyl, and $C_1$ to $C_8$ alkoxyl;

in which $R^2$, $R^3$, and $R^4$ are selected from the group consisting of H, $C_1$ to $C_8$ alkyl, $C_1$ to $C_8$ haloalkyl, and $C_1$ to $C_8$ alkoxyl, whereby a precursor is formed from a substituted ethylene ligand;

in which the compound includes an additive to create a metal precursor blend, the blend further comprising the substituted ethylene has the following structural formula:

$$(R^1)(R^2)C=C(R^3)(R^4)$$

in which $R^1$ is selected from the group consisting of $C_1$ to $C_8$ alkyl, $C_1$ to $C_8$ haloalkyl, and $C_1$ to $C_8$ alkoxyl; and in which $R^2$, $R^3$, $R^4$ are selected from the group consisting of H, $C_1$ to $C_8$ alkyl, $C_1$ to $C_8$ haloalkyl, and $C_1$ to $C_8$ alkoxyl, whereby the precursor is further stabilized in a liquid phase.

6. A metal precursor as in claim 3 in which the metal is selected from the group consisting of copper (Cu), silver (Ag), and iridium (Ir).

7. A metal precursor as in claim 6 in which the additive is 2-methyl-1-butene, at approximately 5.04% by weight of the precursor blend.

8. A metal precursor as in claim 6 in which the substituted ethylene ligand selected to form the precursor is the same substituted ethylene ligand used as the additive to from the precursor blend.

9. A metal precursor as in claim 4 in which the metal is selected from the group consisting of copper, silver, and iridium.

10. A method for synthesizing a metal(hfac) [M(hfac)] substituted ethylene precursor comprising the steps of:
 a) forming a uniformly mixed solution of $M_2O$ in a solvent;
 b) introducing a substituted ethylene to the solution of Step a), and forming a uniformly mixed solution;
 c) introducing hexafluoroacetylacetone (hfac) to the solution of Step b), and forming a uniformly mixed solution;
 d) filtering the solution to remove solid materials, whereby any excess $M_2O$ is removed;
 e) removing the solvent from the solution; and
 f) filtering to remove the solid material, whereby a liquid phase precursor is formed.

11. A method as in claim 10 in which Step b) includes the substituted ethylene being 2-methyl-1-butene.

12. A method as in claim 10 in which Step a) includes the $M_2O$ being, in proportion, 0.120 mol, in which Step b) includes the substituted ethylene being, in proportion, 0.17 mol, and in which Step c) includes the hfac being, in proportion, 0.17 mol.

13. A method as in claim 10 in which Step d) includes removing solid material larger than approximately 25 microns.

14. A method as in claim 13 in which Step d) includes using celite to filter the solution.

15. A method as in claim 10 in which Step a) includes using a solvent selected from the group consisting of dichloromethane and tetrahydrofuran (THF).

16. A method as in claim 10 in which Step f) includes filtering solid material having a size greater than approximately 1 micron.

17. A method as in claim 10 comprising a further step, following Step e), and preceding Step f), of:
 $e_1$) adding less than approximately 10%, by weight ratio, of the substituted ethylene used in Step b) to the solution, whereby the liquid phase stability of the precursor is improved.

18. A method as in claim 17 in which Step $e_1$) includes adding approximately 5.04% substituted ethylene.

19. A method as in claim 10 wherein the metal is selected from the group consisting of copper and silver.

* * * * *